(12) United States Patent
Upadhyay et al.

(10) Patent No.: US 11,508,480 B2
(45) Date of Patent: Nov. 22, 2022

(54) ONLINE PARTIALLY REWARDED LEARNING

(71) Applicant: International Business Machines Corporation, Armonk, NY (US)

(72) Inventors: Sohini Upadhyay, Cambridge, MA (US); Mikhail Yurochkin, Cambridge, MA (US); Mayank Agarwal, Cambridge, MA (US); Djallel Bouneffouf, Wappingers Falls, NY (US); Yasaman Khazaeni, Needham, MA (US)

(73) Assignee: International Business Machines Corporation, Armonk, NY (US)

( * ) Notice: Subject to any disclaimer, the term of this patent is extended or adjusted under 35 U.S.C. 154(b) by 707 days.

(21) Appl. No.: 16/554,344

(22) Filed: Aug. 28, 2019

(65) Prior Publication Data

US 2021/0065897 A1    Mar. 4, 2021

(51) Int. Cl.
| | |
|---|---|
| G16H 50/20 | (2018.01) |
| G16H 10/20 | (2018.01) |
| G06N 3/08 | (2006.01) |
| G06F 17/16 | (2006.01) |
| G06F 16/901 | (2019.01) |
| G06F 17/15 | (2006.01) |
| G06N 20/00 | (2019.01) |

(52) U.S. Cl.
CPC ......... *G16H 50/20* (2018.01); *G06F 16/9024* (2019.01); *G06F 17/15* (2013.01); *G06F 17/16* (2013.01); *G06N 3/084* (2013.01); *G06N 20/00* (2019.01); *G16H 10/20* (2018.01)

(58) Field of Classification Search
None
See application file for complete search history.

(56) References Cited

U.S. PATENT DOCUMENTS

| | | |
|---|---|---|
| 8,909,590 B2 | 12/2014 | Newnham et al. |
| 9,536,191 B1 | 1/2017 | Arel et al. |
| 2006/0206337 A1 | 9/2006 | Paek et al. |

(Continued)

OTHER PUBLICATIONS

Chapelle (edited by), Semi-Supervised Learning, The MIT Press Cambridge, Massachusetts, 2016, cover pages and table of contents pp. i-x, 11 pages, full book of 524 pages access via http://www.acad.bg/ebook/ml/MITPress-%20SemiSupervised%20Learning.pdf.

(Continued)

*Primary Examiner* — Craig C Dorais
(74) *Attorney, Agent, or Firm* — Anthony Curro; Otterstedt & Kammer PLLC

(57) ABSTRACT

A feature vector characterizing a system to be analyzed via online partially rewarded machine learning is obtained. Based on the feature vector, a decision is made, via the machine learning, using an online policy. The system is observed for environmental feedback. In at least a first instance, wherein the observing indicates that the environmental feedback is available, the environmental feedback is obtained. In at least a second instance, wherein the observing indicates that the environmental feedback is missing, the environmental feedback is imputed via an online imputation method. the online policy is updated based on results of the obtained environmental feedback and the online imputation method. A decision is output based on the updated online policy.

20 Claims, 7 Drawing Sheets

---

```
Algorithm 1 ROGCN

1: Input: W₁, W₂, X₀, y₀, A₀
2: Set X = X₀, y = y₀, A = A₀
3: for t = T₀ + 1 to T do
4:     Append xₜ to X, -1 to y
5:     Update A with new edges if graph information is
       available or build k-NN similarity graph from X to
       obtain A
6:     Update W₁ and W₂ through GCN backpropagation
       with inputs X, A, y
7:     Retrieve GCN prediction ŷₜ and observe environment
       response hₜ ∈ {-1, 0, 1} for ŷₜ
8:     if hₜ = 1 then
9:        Replace last entry of y with ŷₜ
10:    end if
11: end for
```

(56) References Cited

U.S. PATENT DOCUMENTS

| | | |
|---|---|---|
| 2018/0374138 A1 | 12/2018 | Mohamed |
| 2019/0042943 A1 | 2/2019 | Dasgupta et al. |
| 2019/0073363 A1 | 3/2019 | Perez et al. |
| 2019/0377819 A1* | 12/2019 | Filliben .................. G06F 16/23 |
| 2020/0108327 A1* | 4/2020 | Ohaco ................... G06N 20/00 |
| 2020/0348641 A1* | 11/2020 | Li ....................... G05B 19/0426 |

OTHER PUBLICATIONS

Kipf et al., Semi-supervised classification with graph convolutional networks, arXiv preprint arXiv:1609.02907 (2016), 14 pages https://arxiv.org/abs/1609.02907.

Li et al., A contextual-bandit approach to personalized news article recommendation, Proceedings of the 19th international conference on World wide web. ACM, 2010, 10 pages htttps://arxiv.org/abs/1003.0146.

Bartok, et al. Partial monitoring—classification, regret bounds, and algorithms, 40 pages http://www.mit.edu/~rakhlin/papers/partial_monitoring.pdf.

Gajane et al., Corrupt bandits for preserving local privacy, arXiv preprint arXiv:1708.05033 (2017), 27 pages https://arxiv.org/abs/1708.05033.

Peter Mell and Timothy Grance, The NIST Definition of Cloud Computing, NIST Special Publication 800-145, Sep. 2011, cover, pp. i-iii and 1-3.

Anonymous Authors, Online Semi-Supervised Learning with Bandit Feedback, 10 pages.

Anonymous Authors, Supplementary material for Online Semi-Supervised Learning with Bandit Feedback, 3 pages.

* cited by examiner

Algorithm 1 ROGCN

1: Input: $W_1, W_2, X_0, y_0, \hat{A}_0$
2: Set $X = X_0, y = y_0, \hat{A} = \hat{A}_0$
3: for $t = T_0 + 1$ to $T$ do
4:     Append $x_t$ to $X$, -1 to $y$
5:     Update $\hat{A}$ with new edges if graph information is available or build $k$-NN similarity graph from $X$ to obtain $\hat{A}$
6:     Update $W_1$ and $W_2$ through GCN backpropagation with inputs $X, \hat{A}, y$
7:     Retrieve GCN prediction $\hat{y}_t$ and observe environment response $h_t \in \{-1, 0, 1\}$ for $\hat{y}_t$
8:     if $h_t = 1$ then
9:         Replace last entry of $y$ with $\hat{y}_t$
10:     end if
11: end for

*FIG. 3*

| Datasets | Instances | Features | Classes |
|---|---|---|---|
| CNAE-9 | 1080 | 856 | 9 |
| Internet Advertisements | 3279 | 1555 | 2 |
| Cora | 2708 | 1433 | 7 |
| Warfarin | 5528 | 91 | 3 |

*FIG. 6*

Algorithm 2 BILINUCB
1: Input: $\alpha$, $b$, $A$, $I(\cdot)$
2: for $t = T_0 + 1$ to $T$ do
3:     Update $I(\cdot)$ with $x_t$ and retrieve $I(x_t) \in \Delta^{K-1}$
4:     for all $k \in K$ do
5:         $\theta_k \leftarrow A_k^{-1} * b_k$        $\theta_k \leftarrow \theta_k / \|\theta_k\|_2$
6:         $\sigma_k \leftarrow \alpha \sqrt{x_t^\top A_k^{-1} x_t}$      $\mu_k \leftarrow \theta_k^\top x_t$
7:     end for
8:     Predict $\hat{y}_t = \mathrm{argmax}_k(\mu_k + \sigma_k)$, and observe environment response $h_t \in \{-1, 0, 1\}$
9:     if $h_t = 1$ then
10:        $A_k \leftarrow A_k + x_t x_t^\top$ for $k = 1, \ldots, K$
11:        $b_{\hat{y}_t} \leftarrow b_{\hat{y}_t} + x_t$
12:        Update $I(\cdot)$ with label $y_t = \hat{y}_t$
13:     else if $h_t = 0$ then
14:        $A_{\hat{y}_t} \leftarrow A_{\hat{y}_t} + x_t x_t^\top$
15:     else if $h_t = -1$ then
16:        $A_{\hat{y}_t} \leftarrow A_{\hat{y}_t} + x_t x_t^\top$
17:        $b_{\hat{y}_t} \leftarrow b_{\hat{y}_t} + r_t(\hat{y}_t, x_t) x_t$ (see Eq. (1))
18:     end if
19: end for

FIG. 4

| % Reward Missing | ILINUCB-Random | BILINUCB-Random |
|---|---|---|
| 25 | 67.29 ± 4.15 | 67.65 ± 4.30 |
| 50 | 65.67 ± 5.20 | 67.19 ± 5.37 |
| 75 | 49.77 ± 4.68 | 56.36 ± 3.71 |

| % Reward Missing | ILINUCB-KMeans | BILINUCB-KMeans |
|---|---|---|
| 25 | 67.92 ± 3.98 | 67.69 ± 4.30 |
| 50 | 67.14 ± 4.84 | 67.37 ± 5.18 |
| 75 | 56.62 ± 4.40 | 57.16 ± 3.57 |

FIG. 8

Algorithm 3 GCNUCB

1: Input: $W_1^{(k)}, W_2^{(k)}, C_k, r_{.,k}, y_0^{(k)} \, \forall k, X_0, \hat{A}_0, \alpha$
2: Set $y^{(k)} = y_0^{(k)} k = 1, \ldots, K, X = X_0, \hat{A} = \hat{A}_0$
3: for $t = T_0 + 1$ to $T$ do
4:     Append $x_t$ to $X$, -1 to each of $y^{(1)}, \ldots, y^{(K)}$
5:     Update $\hat{A}$ with new edges if graph information is available or build $k$-NN similarity graph from $X$ to obtain $\hat{A}$
6:     Update $W_1^{(k)}$ and $W_2^{(k)}$ through GCN backpropagation with inputs $X, \hat{A}, y^{(k)}$ for $k = 1, \ldots, K$
7:     Retrieve embeddings $g(X)_t^{(k)} \, \forall k$
8:     Compute $A_k$ (Eq. (2)) and $\theta_k$ (Eq. (3)) $\forall k$
9:     Make prediction $\hat{y}_t$ using Eq. (4) and observe environment response $h_t$
10:     if $h_t = 1$ then
11:         For each $k$ replace last entry of $y^{(k)}$ with 1 if $\hat{y}_t = k$ and 0 otherwise
12:         Append $t$ to each $C_k$ and 1 to $r_{.,k}$ if $\hat{y}_t = k$ and 0 otherwise
13:     else if $h_t = 0$ (learning from mistakes) then
14:         Replace last entry of $y^{(\hat{y}_t)}$ with 0
15:         Append $t$ to $C_{\hat{y}_t}$ and 0 to $r_{.,\hat{y}_t}$
16:     else if $h_t = -1$ (imputing) then
17:         Append $t$ to $C_{\hat{y}_t}$, output of $\hat{y}_t$-th GCN to $r_{.,\hat{y}_t}$
18:     end if
19: end for

*FIG. 5*

| 25% Missing labels | CNAE-9 | Internet Ads | Warfarin | Cora |
|---|---|---|---|---|
| LINUCB | 67.57 ± 2.90 | 90.08 ± 0.64 | 53.70 ± 0.77 | 38.06 ± 3.45 |
| ROGCN | 64.73 ± 2.67 | 88.22 ± 1.73 | 47.72 ± 9.40 | 48.57 ± 7.75 |
| BILINUCB-GCN | 67.27 ± 2.79 | 89.91 ± 0.73 | 53.70 ± 0.77 | 37.66 ± 3.92 |
| BILINUCB-KMeans | 67.69 ± 4.30 | 90.37 ± 0.63 | 52.53 ± 4.83 | 39.11 ± 2.68 |
| GCNUCB | 77.10 ± 1.89 | 93.14 ± 0.39 | 55.19 ± 3.40 | 66.01 ± 1.35 |

| 50% Missing labels | CNAE-9 | Internet Ads | Warfarin | Cora |
|---|---|---|---|---|
| LINUCB | 64.25 ± 3.55 | 88.62 ± 0.67 | 51.87 ± 5.12 | 38.85 ± 2.74 |
| ROGCN | 65.96 ± 3.69 | 88.38 ± 1.93 | 49.37 ± 8.29 | 47.71 ± 9.25 |
| BILINUCB-GCN | 63.52 ± 3.31 | 88.40 ± 0.73 | 51.75 ± 5.32 | 38.08 ± 2.97 |
| BILINUCB-KMeans | 67.37 ± 5.18 | 89.95 ± 0.66 | 54.20 ± 0.30 | 39.20 ± 1.76 |
| GCNUCB | 74.55 ± 1.82 | 92.62 ± 0.37 | 56.51 ± 3.43 | 63.47 ± 2.26 |

| 75% Missing labels | CNAE-9 | Internet Ads | Warfarin | Cora |
|---|---|---|---|---|
| LINUCB | 61.67 ± 3.16 | 86.66 ± 0.99 | 52.99 ± 2.61 | 33.92 ± 0.04 |
| ROGCN | 65.67 ± 5.28 | 88.31 ± 1.81 | 47.48 ± 5.41 | 49.63 ± 5.06 |
| BILINUCB-GCN | 61.36 ± 3.79 | 86.68 ± 1.04 | 50.04 ± 11.44 | 32.21 ± 5.99 |
| BILINUCB-KMeans | 57.16 ± 3.57 | 88.21 ± 0.99 | 51.21 ± 7.12 | 32.51 ± 4.98 |
| GCNUCB | 70.82 ± 2.33 | 91.45 ± 0.89 | 53.31 ± 2.98 | 58.29 ± 2.80 |

*FIG. 7*

ONLINE PARTIALLY REWARDED LEARNING

BACKGROUND

The present invention relates to the electrical, electronic and computer arts, and more specifically, to machine learning and human-machine dialog.

In many machine learning problems, data is naturally collected over time and systems are required to make predictions (take an action) before they are allowed to observe any response from the environment. Oftentimes, there is no response available, e.g. there is a missing label and/or the environment is not responding to the system's action. Furthermore, in many practical systems, one can only hope to observe feedback indicating whether a given action is "good" or "bad" (1 or 0 reward); the latter case obscuring the true label for learning.

SUMMARY

Principles of the invention provide techniques for online partially rewarded learning. In one aspect, an exemplary method includes the steps of obtaining a feature vector characterizing a system to be analyzed via online partially rewarded machine learning; based on the feature vector, making a decision, via the machine learning, using an online policy; observing the system for environmental feedback; in at least a first instance, wherein the observing indicates that the environmental feedback is available, obtaining the environmental feedback; in at least a second instance, wherein the observing indicates that the environmental feedback is missing, imputing the environmental feedback via an online imputation method; updating the online policy based on results of the obtained environmental feedback and the online imputation method; and outputting a decision based on the updated online policy.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

enhanced accuracy including, e.g., improving reward and/or reducing regret;

enhanced learning for the same number of samples as compared to prior art techniques so desired level of accuracy can be achieved with fewer samples, thus, in at least some embodiments, reducing CPU time to achieve desired accuracy, thereby improving computer performance of a computer implementing machine learning;

using multi-GCN embedded Upper Confidence Bound (GCNUCB) embeddings according to aspects of the invention reduces the dimensionality of the context, enabling faster matrix inversion than LINUCB (Linear Upper Confidence Bound) (an existing method/prior art), thereby reducing computation time and improving computer performance of a computer implementing machine learning;

using a GPU for each GCN (GCN=Graph Convolutional Networks) in GCNUCB allows for parallel computation, reducing computation time and improving computer performance of a computer implementing machine learning.

These and other features and advantages of the present invention will become apparent from the following detailed description of illustrative embodiments thereof, which is to be read in connection with the accompanying drawings.

BRIEF DESCRIPTION OF THE DRAWINGS

FIG. 3 shows a rewarded online graph convolutional network algorithm according to an embodiment of the present invention;

FIG. 4 shows a bounded imputation linear upper confidence bound algorithm according to an embodiment of the present invention;

FIG. 5 shows a multi-graph convolutional network upper confidence bound algorithm according to an embodiment of the present invention;

FIG. 6 presents a table of dataset statistics showing experimental results according to aspects of the invention;

FIG. 7 presents a table of total average accuracy showing experimental results according to aspects of the invention;

FIG. 8 presents a table of CNAE-9 total average accuracy showing experimental results according to aspects of the invention.

DETAILED DESCRIPTION

Figure 1:
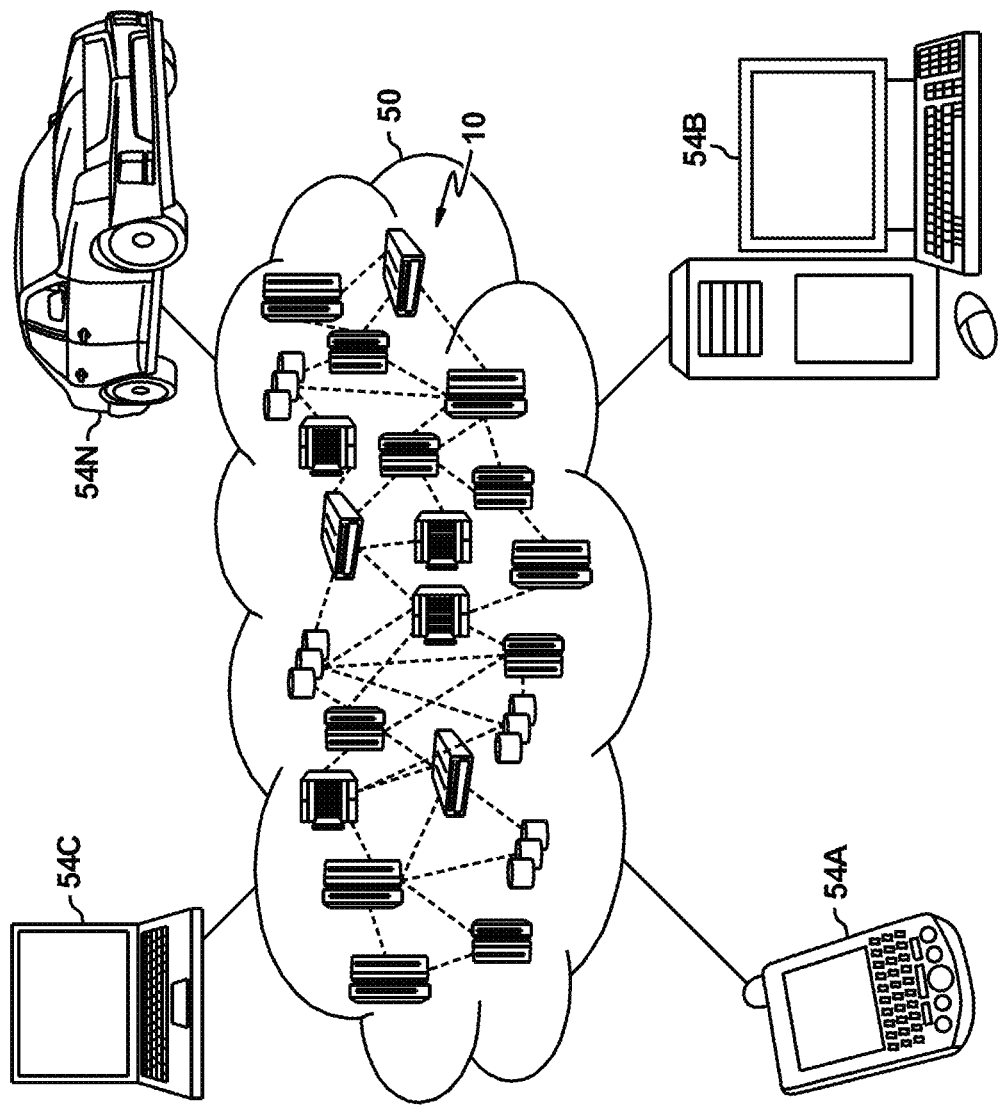
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and RDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
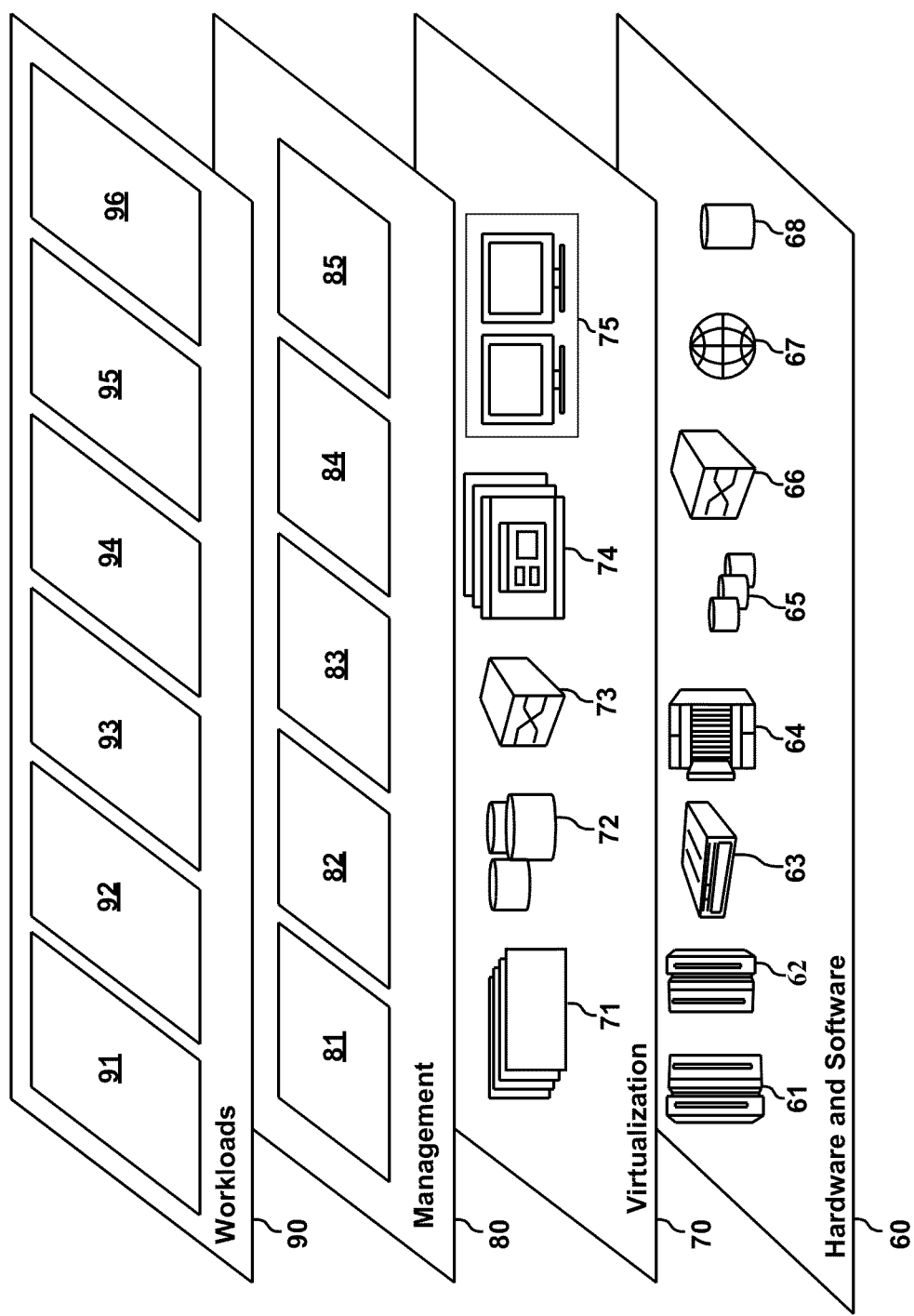
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for Which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and machine learning as a service 96.

One or more embodiments provide techniques for online partially rewarded learning. Many machine learning problems fit into the Online Partially Rewarded (OPR) paradigm. The term "online" in this context refers to the case where data is often naturally collected over time and systems are required to make predictions (take an action) before they are allowed to observe any response from the environment. The term "partially" in this context refers to the aspect that, oftentimes, there is no response available, e.g. there is a missing label and/or the environment is not responding to the systems action. Regarding the term "rewarded," in the context of online (multiclass) supervised learning, it can be assumed that the environment will provide the true label.

However, in many practical systems, one can only hope to observe feedback indicating whether a given action is "good" or "bad" (1 or 0 reward); the latter case obscuring the true label for learning. For example, in clinical trials, reward is partial, as patients may not return for follow up evaluation. When patients do return, if feedback on their treatment is negative, the best treatment, or true label, remains unknown and the only available information is a reward of 0 for the treatment administered. In another example, in dialog systems, a user's query is often directed to a number of domain-specific agents and the best response is returned. If the user provides negative feedback to the returned response, the best available response is uncertain; moreover, users can choose to not provide feedback at all.

Thus, determining how to handle partially rewarded feedback in online systems is an open problem. One or more embodiments advantageously provide an imputation and feedback driven methodology that can make use of the available information to provide accurate decision support.

One or more embodiments are applicable, for example, to machine learning as a service, dialog systems, and/or artificial intelligence (AI) for diagnostics and related health/medical applications.

In one or more embodiments, a feature vector is input to the system and the output is an action and/or decision. In a first step, use the feature vector to make a decision using an online policy. In a second step, observe the environmental response and/or feedback; if missing, employ an online imputation method to impute the response and/or feedback. In a third step, update the online policy used in the first step with the environmental or imputed response and/or feedback, as the case may be.

A number of different algorithms are discussed and evaluated herein. We have found that a multi-GCN embedded Upper Confidence Bound (GCNUCB) algorithm is particularly advantageous in one or more embodiments (GCN=Graph Convolutional Networks). In one or more embodiments, GCNUCB synthesizes elements of semi-supervised Graph Convolutional Neural Networks (GCNs) and the contextual "bandit" algorithm LINUCB (Linear Upper Confidence Bound) to solve the OPR problem. As in the general case, a feature vector is input to the system and the output is an action and/or decision. In a first step, retrieve the GCN embedding of the feature vector and pass this embedding to LINUCB to make a decision. In a second step, observe the environmental response and/or feedback; if missing, employ GCN to impute response and/or feedback. In a third step, update LINUCB with environmental or imputed response and/or feedback; and update the GCN with the environmental response.

One or more embodiments address a new problem at the intersection of semi-supervised learning and contextual "bandits," useful for a number of applications including clinical trials and advertisement recommendations. A Graph Convolutional Network (GCN), a semi-supervised learning approach, can be adjusted to the new problem formulation. One or more embodiments also provide a variant of the linear contextual bandit with semi-supervised missing rewards imputation and establish imputation-agnostic regret bounds. Aspects of both approaches are combined in one or more embodiments to provide a multi-GCN embedded contextual "bandit." Non-limiting exemplary experimental results are also disclosed herein.

Consider the problem of Online Partially Rewarded (OPR) learning, which poses a synthesis of the challenges often considered in the semi-supervised and contextual "bandit" literature.

Practical scenarios that fall under the umbrella of OPR range from clinical trials to dialog orchestration. As noted, in clinical trials, reward is partial, as patients may not return for follow-up evaluation. When patients do return, if feedback on their treatment is negative, the best treatment, or true label, remains unknown and the only available information is a reward of 0 for the treatment administered. In dialog systems, a user's query is often directed to a number of domain-specific agents and the best response is returned. If the user provides negative feedback to the returned response, the best available response is uncertain; moreover, users can choose to not provide feedback at all.

In many applications, obtaining labeled data requires a human expert or expensive experimentation, while unlabeled data may be cheaply collected in abundance. Learning from unlabeled observations to improve prediction performance is a pertinent challenge of semi-supervised learning. One of the possible approaches is the continuity assumption; i.e., points closer to each other in the feature space are more likely to share a label. When the data has a graph structure, another approach is to perform node classification using graph Laplacian regularization, i.e. penalizing differences in outputs of the connected nodes. The latter approach can also be applied without the graph under the continuity assumption by building a similarity based graph. Note that the problem of online semi-supervised leaning has heretofore rarely been considered, with few exceptions. In one or more applications addressed herein, the problem is further complicated by the "bandit-like" feedback in place of labels, rendering the existing semi-supervised approaches inapplicable. We have found that one of the recent approaches, Graph Convolutional Networks (GCN), can be extended to applications addressed herein, using techniques disclosed herein.

The "multi-armed bandit" problem provides a solution to the exploration versus exploitation trade-off, informing a player how to pick within a finite set of decisions while maximizing cumulative reward in an online learning setting. Optimal solutions have been developed for a variety of problem formulations. These approaches do not take into account the relationship between context and reward, potentially inhibiting overall performance. In Linear Upper Confidence Bound (LIN-UCB) and in Contextual Thompson Sampling (CTS), a linear dependency is assumed between the expected reward of an action and its context; the representation space is modeled using a set of linear predictors. These algorithms assume that the "bandit" can observe the reward at each iteration, which is not the case in one or more applications addressed herein. Several authors have considered variations of partial and/or corrupted rewards; however, it is believed that the case of entirely missing rewards has not heretofore been addressed.

One or more embodiments address the handling of the problem of online semi-supervised learning with "bandit" feedback. One or more embodiments provide extensions to existing methods in the respective domains to accommodate issues addressed herein. One or more embodiments combine the strengths of both approaches, using techniques disclosed herein, to arrive at an algorithm well suited for the Online Partially Rewarded learning problem. A theoretical analysis of regret bounds of LINUCB with a missing reward variant is provided and verified experimentally.

Consider two approaches coming from the respective domains of semi-supervised learning and "contextual bandits," as well as their relevance and shortcomings in solving the OPR problem.

Graph Convolutional Networks: Neural networks have proven to be powerful feature learners when classical linear approaches fail. The classical neural network, Multi-Layer Perceptron (MLP), is dramatically over-parameterized and requires copious amounts of labeled data to learn. On the other hand, Convolutional Neural Networks (CNNs) are more effective in the image domain, partially due to parameter sharing exploiting relationships between pixels. Image structure can be viewed as a grid graph where neighboring pixels are connected nodes. This perspective and the success of CNNs inspired the development of convolution on graphs neural networks based on the concept of graph convolutions known in the signal processing communities. Though all these works are in the realm of classical supervised learning, the idea of convolving a signal over graph nodes is also widely applied in semi-supervised (node classification) learning, where the graph describes relationships among observations (consider also a grid graph of features (pixels) in CNNs). A Graph Convolutional Network (GCN) provides an elegant synthesis of convolution on graphs ideas and neural network feature learning capability, which significantly outperformed prior semi-supervised learning approaches on several citation networks and knowledge graph datasets.

To understand the GCN method, let $X \in R^{T \times D}$ denote a data matrix with T observations and D features and let A denote a positive, sparse, and symmetric adjacency matrix A of size T×T. The GCN embedding of the data with one hidden layer of size L is $g(X) = \hat{A}\ ReLU(\hat{A} \times W) \in R^{T \times L}$ where $\hat{A}$ is degree normalized adjacency with self connections: $\hat{A} = (\mathcal{D} + \mathcal{I}_\mathcal{J})^{-1/2}(A + \mathcal{I}_\mathcal{J})(\mathcal{D} + \mathcal{I}_\mathcal{J})^{-1/2}$ and $\mathcal{D}_{ii} = \Sigma_{j=1}^T A_{ij}$ is the diagonal matrix of node degrees. $W \in R^{D \times L}$ is a trainable weight vector. Resulting embedded data goes into the softmax layer and the loss for back-propagation is computed only on the labeled observations. The product $\hat{A}$ X gives the one-hop convolution—signal from a node is summed with signals from all of its neighbors achieving smooth transitions of the embeddings g(X) over the data graph. Although a powerful semi-supervised approach, GCN is not suitable for the Online and Rewarded components of OPR. It additionally requires a graph as an input, which may not be available in some cases.

Contextual Bandit: The contextual bandit problem is defined as follows. At each time $t \in \{1, \ldots, T\}$, a player is presented with a context vector $x_t \in R^D$, $\|x_t\| \leq 1$ and must choose an arm $k \in \{1, \ldots, K\}$. The parameter $r_{t,k} \in [0, 1]$ is the reward of the action k at time t, and $r_t \in [0, 1]^K$ denotes a vector of rewards for all arms at time t. One or more embodiments operate under the linear realizability assumption, i.e., there exist unknown weight vectors $\theta_k^* \in R^D$ with $\|\theta_k^*\|_2 \leq 1$ for $k=1, \ldots, K$ so that $$\forall k,t: \mathbb{E}_{[r_{t,k}|x_t]} = \theta_k^{*T} x_t$$

Hence, the $r_{t,k}$ are independent random variables with expectation $x_t^T \theta_k^*$ One solution to the contextual bandit problem is the LIN-UCB algorithm where a pertinent idea is to apply online ridge regression to incoming data to obtain an estimate of the coefficients $\theta_k$ for $k=1, \ldots, K$. At each step t, the LINUCB policy selects the arm with the highest upper confidence bound of the reward $k(t) = \text{argmax}_k (\mu_k + \sigma_k)$, where $\mu_k = \theta_k^T x_t$ is the expected reward for arm k, $$\sigma_k = \alpha \sqrt{x_t^\top A_k^{-1} x_t}$$

is the standard deviation of the corresponding reward scaled by exploration-exploitation trade-of parameter $\alpha$ (chosen a priori) and $A_k$ is the covariance of the k-th arm context. LINUCB requires a reward for the chosen arm, $r_{t,k(t)}$, to be observed to perform its updates. In some applications, reward may not be available at every step t, hence one or more embodiments adjust the LINUCB algorithm to learn from data with missing rewards.

The Online Partially Rewarded (OPR) problem will now be formally defined and a series of algorithms are presented, starting with natural modifications of GCN and LINUCB to suit the OPR problem setting. An algorithm building on strengths of both GCN and LINUCB is presented.

Formal definitions of each of the OPR keywords are now provided:

Online: at each step $t=1, \ldots, T$ observe observation $x_i$ and seek to predict its label $\hat{y}_t$ using $x_t$ and possibly any information obtained prior to step t.

Partially: after the prediction $\hat{y}_t$ is made, the environment may not provide any feedback (for example use −1 to encode absence of feedback) and proceed to step t+1 without knowledge of the true $y_t$.

Rewarded: suppose there are K possible labels $y_t \in \{1, \ldots, K\}$. The environment at step t, if it responds to the prediction $\hat{y}_t$, will not provide true $y_t$, but instead a response $h_t \in \{-1, 0, 1\}$, where $h_t = 0$ indicates $\hat{y}_t \neq y_t$ and $h_t = 1$ indicates $\hat{y}_t = y_t$ (−1 indicates missing response).

Note on absence of environment response: Assume for illustrative purposes that there is no dependence on $x_t$ in whether the environment will respond or not. This is a common setting in semi-supervised learning. Access is available to limited samples from the joint distribution of data and labels P(x,y) and a larger amount of samples from the data marginal P(x) with the goal to infer P(y|x) using both. This assumption is appropriate in some applications of interest, e.g., whether user will provide feedback to the dialog agent is independent of what the user asked.

Rewarded Online CCN: Consider three challenges to be addressed to formulate Rewarded Online GCN (ROGCN): (i) online learning; (ii) the environment only responds with 0 or 1 to predictions and (iii) the potential absence of graph information. As will be seen, there is a natural path from GCN to ROGCN. Suppose there is a small portion of data and labels available from the start, $X_0 \in R^{T_0 \times D}$ and $y_0 \in \{-1, 1, \ldots, K\}^{T_0}$, where D is the number of features, K is the number of classes and To is the size of initially available data. When there is no graph available, a k-NN graph (k is a parameter chosen a priori) can be constructed based on similarities between observations. This approach is common in convolutional neural networks on feature graphs and is adopted herein for graph construction between observations $X_0$ to obtain graph adjacency $A_0$. With $X_0$, $y_0$, $A_0$, it is possible to train GCN with L hidden units (a parameter chosen a priori) to obtain initial estimates of hidden layer weights $W_1 \in R^{D \times L}$ and softmax weights $W_2 \in R^{L \times K}$. Next, start to observe the stream of data—as new observation $x_t$ arrives, add it to the graph and data matrix, and append −1 (missing label) to y. Then run additional training steps of GCN and output a prediction to obtain the environmental response $h_t \in \{-1, 0, 1\}$. Here 1 indicates a correct prediction, hence it is included in the set of available labels for future predictions; 0 indicates a wrong prediction; and −1 an absence of a response. In the latter two cases, continue to treat the label of $x_t$ as missing. This procedure is summarized in Algorithm 1 of FIG. 3.

Bounded Imputation LINUCB: Contextual multi-armed "bandits" offer a powerful approach to online learning when true labels are not available and the environment's response to a prediction is observed at every observation instead. However, in the OPR problem setting, the environment may not respond to the agent for every observation. The classic "bandit" approach such as Linear Upper Confidence Bound (LINUCB) may be directly applied to OPR; however, it would not be able to learn from observations without environmental response. One or more embodiments combine LINUCB with a user-defined imputation mechanism for the reward when environment response is missing. In order to be robust to variations in the imputation quality, one or more embodiments only allow the imputed reward to vary within the agent's beliefs. To make use of the context in the absence of the reward, one or more embodiments consider a user defined imputation mechanism $I(\bullet): R^D \rightarrow \Delta^{K-1}$, which is expected to produce class probabilities for an input context $x_t$ to impute the missing reward. Typically, any imputation mechanism will have an error of its own, hence the imputed reward is constrained to be within one standard deviation of the expected reward for the chosen arm:

$$r_t(k,x_t) = \max(\mu_k - \sigma_k, \min(I(x_t)_k, \mu_k + \sigma_k)). \quad \text{(Eq. 1)}$$

As in ROGCN, one can take advantage of small portion of data to initialize bandit parameters $b_k = \Sigma_{t:y_t=k}^{T_0} x_t$ and $A_k = \Sigma_{t:y_t \neq -1}^{T_0} x_t x_t^\perp$ for k=1, ..., K. Bounded Imputation LINUCB (BILINUCB) is summarized in Algorithm 2 of FIG. 4. Below, regret bounds are established for the BILINUCB, which are superior to LINUCB regret bounds.

Multi-GCN embedded UCB: Two algorithms have been presented for OPR learning; however, both approaches pose some limitations: ROGCN is unable to learn from misclassified observations and has to treat them as missing labels, while BILINUCB assumes a linear relationship between data features and labels, and even with perfect imputation, is limited by the performance of the best linear classifier. Note that the "bandit" perspective allows one to learn from misclassified observations, i.e. when the environment response $h_t=0$, and the neural network perspective facilitates learning better features such that a linear classifier is sufficient. This observation leads to development of a more sophisticated synthesis of GCN and LINUCB approaches, where advantages of both perspectives are combined.

To begin, note that if K=2, an $h_t=0$ environment response identifies the correct class; hence, the OPR reduces to online semi-supervised learning for which GCN can be trivially adjusted using ideas from ROGCN. To take advantage of this for K>2 consider a suite of GCNs for each of the classes, which then necessitates a procedure to decide which of the GCNs to use for prediction at each step. One or more embodiments use a suite of class-specific GCNs, where prediction is made using a contextual "bandit" with a context of the k-th arm coming from the hidden layer representation of the k-th class GCN and, when missing, the reward is imputed from the corresponding GCN.

The multi-GCN embedded Upper Confidence Bound (GCNUCB) "bandit" is now described in more detail. Let $g(X)^{(k)} = \hat{A} \text{ReLU}(\hat{A} X W_1^{(k)})$ denote the k-th GCN data embedding and let $g(X)_t^{(k)}$ denote the embedding of observation $x_t$. This embedding (additionally normalized to unit $l_2$ norm) is used as context for the corresponding arm of the contextual "bandit." The advantage of this embedding is its graph convolutional nature coupled with expressive power of neural networks. Note that as new observation $x_{t+1}$ is added to the graph and update weights of the GCNs, the embedding of the previously observed $x_1, \ldots, x_t$ evolves. Therefore, instead of dynamically updating "bandit" parameters $b_k$ and $A_k$ as was done in BILINUCB, maintain a set of indices for each of the arms $C_k = \{t: \hat{y}_t = k \text{ or } h_t = 1\}$. At any step, the corresponding "bandit" context covariance and weight estimate can be computed using current embedding:

$$A_k = \Sigma_{t \in C_k} g(X)_t^{(k)} g(X)_t^{(k)\perp} \quad \text{(Eq. 2)}$$

$$\theta_k = A_k^{-1} \Sigma_{t \in C_k} r_{t,k} g(X)_t^{(k)}, \theta_k = \theta_k / \|\theta_k\|_2 \quad \text{(Eq. 3)}$$

where $r_{t,k}$ is the reward that was observed or imputed at step t for arm k (recall that imputing is being done using prediction of the binary GCN corresponding to the arm chosen by the "bandit"). Now the expected value and standard deviation can be computed for the reward on each arm. The prediction is made based on the upper confidence bounds for the rewards of the arms:

$$\mu_k = \theta_k^\perp g(X)_t^{(k)}$$

$$\sigma_k = \alpha \sqrt{g(X)_t^{(k)\perp} A_k^{-1} g(X)_t^{(k)}}$$

$$\hat{y}_t = \text{argmax}_k (\mu_k + \sigma_k). \quad \text{(Eq. 4)}$$

Then observe the environment response $h_t \in \{-1, 0, 1\}$. Unlike ROGCN, GCNUCB is able to learn from mistakes, i.e. when $h_t=0$—although as before the true class is not known, one can be sure that it was not $\hat{y}_t$, hence, use this information to improve GCN corresponding to the class $\hat{y}_t$. GCNUCB is summarized in Algorithm 3 in FIG. 5. Similarly to ROGCN and BILINUCB, one can use a small amount of data $X_0$ and labels $y_0$ converted to binary labels $y_0^{(k)} \in \{-1, 0, 1\}^{T_0}$ (as before −1 encodes missing label) for each class k to initialize GCNs weights $W_1^{(k)}$, $W_{12}^{(k)}$ for k=1, ..., K and index sets $C_k$ for each of the arms k=1, ..., K. The adjacency matrix, if not given, is obtained as in ROGCN.

Regret bounds of BILINUCB: Consider analysis of a modified version of BILINUCB, where it is assumed that the imputation mechanism is unbiased and yields bounded imputed rewards whose variance $\lambda^2$ could be significantly higher than the variance of the actual rewards $\sigma^2$ obtained from feedback. In particular, assume:

$$\text{Var}(r_{t,k} \mid x_t) \leq \begin{cases} \lambda^2 & \text{for imputed feedback} \\ \sigma^2 & \text{for actual feedback} \end{cases} \quad \text{(Eq. 5)}$$

In one or more embodiments, "rewards" can include, e.g., user feedback regarding the suitability of the system-generated decision; and "regret," in essence, refers to how much reward has been missed out on. In one or more embodiments, in order to compute the upper and lower bounds on the expected reward/regret, an assumption is made about the distribution of the rewards. In one or more embodiments, the noise on the rewards is assumed to be heteroscedastic (non-uniform, i.e. not the same across every instance of reward), since the variance of the reward depends on the type of feedback observed (actual or imputed). Now, upper-bound the regret of BILINUCB. The General Contextual "Bandit" Problem (CBP) setting assumes one context per arm instead for BILINUCB setting with the same context shared across arms. To upper-bound the regret of BILINUCB, cast the setting as a general CBP setting in the following way. Choose a global vector $\theta$ as the concatenation of the K vectors, so $\theta=[\theta 1, \ldots, \theta_K]$. Next, define a context $X_{t,k}$ per arm as $x_{t,k}=[\ldots, 0, x_t, 0, \ldots]^T$ with $x_t$ being the k-th vector within the concatenation. Let $S_T = \mathcal{I}_D + \Sigma_{t \in s} x_t x_t^\perp$, where $s \subset \{1, \ldots, T\}$ contains the contexts with missing rewards up to step T, and let $A_T = S_T + \Sigma_{t \notin s} x_t x_t^\perp$.

Definition 1 (Cumulative regret in OPR setting): The regret of an algorithm accumulated during T iterations is given as:

$$R(T) = \sum_{t=1}^{T-|s|} r_{t,k^*(t)} - \sum_{t=1}^{T-|s|} r_{t,k(t)}$$

where $k^*(t) = \text{argmax}_k \theta_k^{*\perp} x_t$ is the best action at step t according to $\theta_1^*, \ldots, \theta_K^*$. Consider the following theorem regarding the regret bound up to step T:

Theorem 1: With probability $1-\delta$, where $0<\delta<1$, $\rho_t>0$, with $\|x_t\| \leq 1$ and $\|\theta^*\| \leq 1$, the upper bound on the R(T) for the BILINUCB in OPR setting, K arms and D features (context size) is given as follows:

$$R(T) \leq \left( \text{Max}_{t \in T}(\rho_t) \sqrt{D \log\left(\frac{\det(A_{T-|s|})^{1/2}}{\delta \det(S_{T-|s|})^{1/2}}\right)} + \|\theta^*\|_2 \right) \quad \text{(Eq. 6)}$$

$$\sqrt{18(T - |s|) \log \frac{\det(A_{T-|s|})}{\det(S_{T-|s|})}}$$

The proof is set forth below. Theorem 1 shows that, if the rewards coming from the imputation mechanism have the same variance as the observed rewards ($\sigma=\lambda$) BILINUCB will have a better upper bound as compared to the LINUCB, where in LINUCB the upper bound has $\log \det(A_{T-|s|})$ under the square root where one has $$\log \frac{\det(A_{T-|s|})}{\det(S_T)}$$

and by Weyl's inequality in matrix theory for perturbation of Hermitian matrices one can say that $$\log \frac{\det(A_{T-|s|})}{\det(S_{T-|s|})} \leq \log \det(A_{T-|s|})$$

(more details are set forth below).

Regarding the just-mentioned proof, $-$let $\rho: X \to R$ be a continuous, positive function, such that $n_t$ is conditionally $\rho(x_t)$-subgaussian, that is for all $t \geq 1$ and $\rho_t = \rho(x_t)$, $$\forall \lambda \in R, E[e^{\lambda n_t} \mid x_t] \leq \exp\left(\frac{\lambda^2 \rho_t^2}{2}\right). \quad \text{(Assumption (1))}$$

Note that this condition implies that the noise has zero mean. Since heteroscedastic noise is to be faced, one or more embodiments also employ the following lemma 1, which is adopted from theorem 2 in Abbasi-Yadkori et al., 2011, supra, with the noise being heteroscedastic.

Lemma 1: Assume that, the measurement noise $n_t$ satisfies Assumption (1). With probability $1-\delta$, where $0<\delta<1$ and $\theta^*$ lies in the confidence ellipsoid.

$$C_t = \left\{ \theta : \|\theta - \hat{\theta}_t\|_{A_t} \leq c_t := \rho_t \sqrt{D \log \frac{\det(A_t)^{1/2} \det(S_t)^{-1/2}}{\delta}} + \|\theta^*\|_2 \right\}$$

To prove lemma 1, follow the same step as Abbasi-Yadkori et al., 2011 supra in the proof of theorem 1, the main difference is that Abbasi-Yadkori et al., 2011, supra has $A_T = \lambda \mathcal{J}_D + \Sigma_{t=1}^T x_t x_t^\perp$ whereas herein $A_T = S_T + \Sigma_{t \notin s} x_t x_t^\perp$ with $S_T = \mathcal{I}_D + \Sigma_{t \in s} x_t x_t^\perp$ with $s \subset T$ contains the contexts with missing rewards.

Now prove theorem 1: following the same step as the proof of theorem 2 in Abbasi-Yadkori et al., 2011, supra, note the following, $$R(t) \leq (2c_t)\|x_t\|_{A_t^{-1}}$$

Since $x^\perp \theta_t^* \in [-1, 1]$ for all $x \in X_t$ then we have $R(t) \leq 2$. Therefore, $$R(t) \leq \min\{(2c_t)\|x\|_{A_t^{-1}}, 2\} \leq 2(c_t) \min\{\|x\|_{A_t^{-1}}, 1\}$$

Therefore, $$[R(t)]^2 \leq 4c_t^2 \min\{\|x\|_{A_t^{-1}}^2, 1\}$$

obtain, $$R(T) \le \sqrt{(T-|s|) \sum_{t=1}^{(T-|s|)} [R(t)]^2} = \sqrt{\sum_{i=1}^{(T-|s|)} 4c_t^2 \min\{\|x\|_{A_T^{-1}}^2, 1\}}$$

$$R(T) \le 2c_{(T-|s|)}\sqrt{(T-|s|)} \sqrt{\sum_{t=1}^{(T-|s|)} \min\{\|x\|_{A_T^{-1}}^2, 1\}},$$

with $c_{(T-|s|)}$ monotonically increasing, since $x \le 2\log(1+x)$ for $x \in [0, 1]$ obtain $$\sum_{t=1}^{(T-|s|)} \min\{\|x\|_{A_T^{-1}}^2, 1\} \le 2 \sum_{t=1}^{(T-|s|)} \log(1 + \|x\|_{A_T^{-1}}^2) \le$$

$$2(\log \det(A_{(T-|s|)}) - \log \det(S_{(T-|s|)})).$$

Use the fact that $A_T = S_T + \Sigma_{s=1}^T x_s x_s^{-1}$ to obtain the last inequality.

$$R(T) \le 2c_{(T-|s|)} \sqrt{2(\text{logdet}(A_{(T-|s|)}) - \text{logdet}(S_{(T-|s|)}))}$$

by upper bounding $C_{(T-|s|)}$ using lemma 1 obtain the result.

Corollary 1: With probability $1-\delta$, where $0<\delta<1$ with $\|x_t\| \le 1$ and $\|\theta^*\| \le 1$, the upper bound on the R(T) for the LINUCB in OPR selling, K arms and D features text size) is given as follows:

$$R(T) \le \frac{(R\sqrt{D\text{logdet}(A_{T-|s|})^{1/2}} + \|\theta^*\|_2)}{\sqrt{18(T-|s|)\text{logdet}(A_{T-|s|})}} \quad \text{(Eq. 7)}$$

The proof is straightforward, by following the same steps as the proof of theorem 2 in Abbasi-Yadkori, Y., Pál, D., and Szepesvári, C., Improved algorithms for linear stochastic bandits, in *Advances in Neural Information Processing Systems*, pp. 2312-2320, 2011, with $T=T-|s|$, since the LINUCB is not generating regret during $|s|$ iteration as it is shown in definition 1.

Experimental results: Note that these results are presented for illustrative purposes and other embodiments might have different results. The results compare the baseline method LINUCB, which ignores the data with missing rewards, to ROGCN, BILINUCB and GCNUCB—algorithm disclosed herein. Four different datasets are considered: CNAE-9 and Internet Advertisements from the UCI Machine Learning Repository; Cora; and Warfarin (blood thinner dosing, a common dataset used for bandit problems). Cora is naturally graph structured data which can be utilized by ROGCN, BILINUCB with ROGCN-based imputation and GCNUCB. For other datasets a 5-NN graph built online from the available was used data as follows.

Suppose at step t data points $x_i \in R^D$ have been observed for $i=1, \ldots, t$. Weights of the similarity graph are computed follows:

$$A_{ij} = \exp\left(\frac{\|x_i - x_j\|_2^2}{\sigma^2}\right) \quad \text{(Eq. 8)}$$

As it was done in Defferrard, M., Bresson, X., and Vandergheynst, P., Convolutional neural networks on graphs with fast localized spectral filtering, in *Advances in Neural information Processing Systems*, pp. 3844-3857, 2016, set $$\sigma = \frac{1}{t} \sum_{i=1}^{t} d(i, i_k),$$

where $d(i, i_k)$ denotes the $L_2$ distance between observation i and its k-th nearest neighbor indexed $i_k$. The k-NN adjacency A is obtained by setting all but k (excluding itself) corresponding closest entries of $A_{ij}$, i, j=1, . . . , t to and symmetrizing. Then, add self connections and row normalize $\hat{A} = (\mathcal{D} + \mathcal{I}_T)^{-1/2} (A + \mathcal{I}_T)(\mathcal{D} + \mathcal{I}_T)^{-1/2}$, where is $\mathcal{D}_{ii} = \Sigma_{j=1}^T A_{ij}$ is the diagonal matrix of node degrees.

For pre-processing, features with large magnitudes were discarded (3 features in Internet Advertisements and 2 features in Warfarin) and all observations were row normalized to have unit $l_1$ norm. Datasets details are summarized in the table of FIG. 6.

For all algorithms that use GCN, default parameters of the GCN and Adam optimizer were used. Default parameters are as follows: 16 hidden units, learning rate of 0.01, 0.0005 weight decay, and dropout of 0.5.

To emulate the OPR setting, we randomly permuted the order of the observations in a dataset and removed labels for some portion (we experimented with three settings: 25%, 50% and 75% missing labels) of the observations chosen at random. For all methods we considered initial data $X_0$ and $y_0$ to represent a single observation per class chosen randomly ($T_0$=K). At a step $t=T_0+1, \ldots, T$ each algorithm is given a feature vector $x_t$ and ought to make a prediction $\hat{y}_t$. The environment response $h_t \in \{-1, 0, 1\}$ is then observed and the algorithm(s) moves onto step t+1. To compare performance of different algorithms at each step t, we compared $\hat{y}_t$ to the true label $y_t$ available from the dataset (but concealed from the algorithms themselves) to evaluate running accuracy. Defined as such, accuracy is inversely proportional to regret.

Imputation Methods: We tested two different imputation functions I(•) for BILINUCB—a ROGCN and simple k-means clustering with 10 clusters. Henceforth, these two approaches are denoted as BILINUCB-GCN and BILINUCB-KMeans. In BILINUCB-GCN, ROGCN was updated with incoming observations and the softmax class prediction was used to impute the missing reward when needed. In BILINUCB-KMeans, the mini-batch k-means algorithm was used to cluster incoming observations online and impute the missing reward with the average non-missing reward of all observations in the corresponding cluster.

Running accuracy results: It was observed that BILINUCB with both imputation approaches and GCNUCB are more robust to data ordering when baseline LINUCB was used for the first three hundred steps and then proceeded with the corresponding algorithm (see FIG. 7 where the aforementioned algorithms and LINUCB perform the same until three hundred samples have been observed and then have individual running accuracies). Thus, in one or more embodiments, the new methods disclosed herein are not used until three hundred samples have been observed. For all LINUCB based approaches, an exploration-exploitation trade-off parameter $\alpha=0.25$ was used. Results are summarized in the table of FIG. 7. Since ordering of the data can affect the problem difficulty, we performed ten data resamplings for each setting to obtain error bars.

It was observed that GCNUCB outperforms the LINUCB baseline and the other tested methods in all of the experiments, indicating that a method synthesizing the exploration capabilities of "bandits" coupled with the effective feature representation power of neural networks is the best solution to the OPR problem in one or more embodiments. The greatest increase in accuracy is seen between GCNUCB and the alternative approaches on the Cora dataset which has a natural adjacency matrix. This suggests that GCNUCB has a particular edge in OPR applications with graph structure. Such problems are Ubiquitous. Consider the non-limiting example of dialog systems—for dialog systems deployed in social network or workplace environments, there exists a graph structure between users, and user information can be considered alongside queries for personalization of responses.

Role of bounding the imputed reward: Notice that on average, a BILINUCB method outperforms LINUCB and ROGCN, with the former result affirming Theorem 1. The proof of Theorem 1, which demonstrates that BILINUCB has better regret bounds than. LINUCB, hinges on bounding the imputed reward as defined in. Equation 1. To understand the role of these imputation bounds and experimentally evaluate Theorem 1 and Corollary 1, the effects of random imputation were analyzed. This use of random imputation is denoted as BILINUCB-Random and ILINUCB-Random as the same without bounding the imputed reward. BILINUCB-KMeans and ILINUCB-KMeans are defined similarly. The overall accuracy of each method on CNAE-9 is summarized in the table of FIG. 8.

As the purpose of these bounds in one or more embodiments is to correct for errors in the imputation method, one might expect to see its impact the most when imputation is inaccurate. This is exactly what is noted in the in the table of FIG. 8. When using a reasonable imputation method, k-means, the imputation bounds do not improve, or only make slight improvements to the results. The improvement gain is much more evident with random imputation, and across both imputation methods, the bounds have a larger impact when there is more reward missing.

Visualizing GCNUCB context space: Recall that the context for each arm of GCNUCB is provided by the corresponding binary GCN hidden layer. The motivation for using binary GCNs to provide the context to LINUCB is the ability of GCN to construct more powerful features using graph convolution and neural networks expressiveness. To see how this procedure improves upon the baseline LINUCB utilizing input features as context, the context and the corresponding bandit weight vectors, $\theta_1, \ldots, \theta_K$, for both LINUCB and GCNUCB were projected to a 2-dimensional space using t-SNE as described in Maaten, L. v. d. and Hinton, G., Visualizing data using t-sne, *Journal of machine learning research*, 9 (November):2579-2605, 2008. In this experiment, the CNAE-9 dataset was analyzed with 25% missing labels. Recall that the "bandit" makes predictions based on the upper confidence bound of the regret: $\text{argmax}_k (\theta_k^\perp x_{k,t} + \sigma_k)$ and that $X_{k,t} = x_t \, \forall k=1, \ldots, K$ for LINUCB and $x_{k,t} = g(X)_t^{(k)}$ for GCNUCB. To better visualize the quality of the learned weight vectors, for this experiment set $\alpha=0$ and hence $\sigma_k = 0$ resulting in a greedy "bandit," always selecting an arm maximizing expected reward $\theta_{tk}^T x_{t,k}$. In this case, a good combination of contexts and weight vectors is the one where observations belonging to the same class are well clustered and a corresponding "bandit" weight vector is directed at this cluster. For LINUCB (68% accuracy) the bandit weight vectors mostly point in the direction of their respective context clusters; however, the clusters themselves are scattered, thereby inhibiting the capability of LINUCB to effectively distinguish between different arms given the context. In the case of GCNUCB (77% accuracy), the context learned by each GCN is tightly clustered into two distinguished regions—one with context for corresponding label and binary GCN when it is the correct label, and the other region with context for the label and GCN when a different label is correct. The tighter clustered contexts allow GCNUCB to effectively distinguish between different arms by assigning higher expected reward to contexts from the correct binary GUN than others, thereby resulting in better performance of GCNUCB than other methods.

It will thus be appreciated that the problem of Online Partially Rewarded (OPR) learning, which combines challenges from semi-supervised learning and multi-armed contextual "bandits," is addressed by one or more embodiments. ROGCN and BILINUCB can be used in one or more instances to solve the OPR problem. The GCNUCB algorithm provides an efficient synthesis of the strengths of the two approaches. Experiments show that in one or more embodiments, GCNUCB, which combines the feature extraction capability of the graph convolution neural networks and natural ability of contextual "bandits" to handle online learning with reward (instead of labels), is the best approach for OPR across a LINUCB baseline and other possible algorithms. One or more embodiments provide tighter clustering, and thus better decision making, as compared to prior art techniques.

One or more embodiments thus address a partially rewarded scenario in online learning. One or more embodiments are not limited to deep reinforcement learning and decision processes with state action sequences, nor are they limited to the application of purchase recommendations. One or more embodiments can handle the case of entirely missing rewards. The dialog and health domains are well suited to application of one or more embodiments. For example, in clinical trials, reward is partial, as patients may not return for follow up evaluation. When patients do return, if feedback on their treatment is negative, the best treatment, or true label, remains unknown and the only available information is a reward of 0 for the treatment administered. In another example, in dialog systems, a user's query is often directed to a number of domain-specific agents and the best response is returned. If the user provides negative feedback to the returned response, the best available response is uncertain and moreover, users can choose to not provide feedback at all.

Given the discussion thus far, it will be appreciated that, in general terms, an exemplary method, according to an aspect of the invention, includes the steps of obtaining a feature vector characterizing a system to be analyzed via online partially rewarded machine learning; based on the feature vector, making a decision, via the machine learning, using an online policy; observing the system for environmental feedback (which can alternatively be referred to as environmental response); and, in at least a first instance, wherein the observing indicates that the environmental feedback is available, obtaining the environmental feedback. Further steps include, in at least a second instance, wherein the observing indicates that the environmental feedback is missing, imputing the environmental feedback via an online imputation method; updating the online policy based on results of the obtained environmental feedback and the online imputation method; and outputting a decision (which can alternatively be referred to as an action) based on the updated online policy.

In a dialog system, feature vectors include, e.g., what the user is asking the dialog system (a representation of the user's query); and the decision includes, e.g., a response to the user's query. In a medical context, feature vectors include, e.g., patient medical history, medication dosage (current and/or historical), height, weight, and the like; and the decision includes, e.g., dosage, whether trial medication is harmful or helpful, etc. Examples of online policies include, e.g., a bandit, online GCN, and the like. Examples of environmental responses include, in the dialog system, whether the answer provided to the user's question receives a "thumbs up" or "thumbs down"; in the medical system, whether the patient has a positive or negative reaction.

One or more embodiments are applicable to a variety of systems; for example, the system can be a medical system conducting clinical trials; a human-machine dialog system; a medical diagnostic system; or the like. These examples are non-limiting and embodiments can be applied to any kind of decision processes where the correct choice is not known and a response/feedback is missing; e.g., showing a subject an advertisement and attempting to determine whether the subject has a positive or negative reaction to it; making movie recommendations; and the like. A medical diagnostic system could include a computer using machine learning to aid in diagnosis of disease. A medical system conducting clinical trials could include a computer using machine learning to aid in determining whether medicines/treatments that are being tried in a clinical setting are effective. A human-machine dialog system could include an interactive voice response system implemented with a computer, acoustic front end, microphone or other transducer, and the like.

It will be appreciated that some embodiments thus include techniques for medical treatment. For example, when a medical diagnostic system using techniques herein indicates that a dosage of medicine should be increased, decreased, or changed to a different medication, the patient's treatment can be changed accordingly. Furthermore, when a system conducting clinical trials indicates that the therapy/medicine being tried is helpful, treatment for those in the trial can be continued and/or other patients not in the trial can be treated with the tested therapy/medicine. Conversely, when a system conducting clinical trials indicates that the therapy/medicine being tried is not helpful, treatment for those in the trial can be stopped and/or other patients not in the trial can be treated with conventional treatments rather than the newly tested therapy/medicine.

In some cases, the ROGCN algorithm (Algorithm 1 of FIG. 3) is employed. ROGCN does not use a bandit algorithm; rather, GCN is used for both decision and imputation, and in this context, GCN handles missing rewards instead of missing labels. Thus, in some instances, the imputing and the making of the decision include applying a rewarded online graph convolutional network by updating weights of the online policy via graph convolutional network backpropagation.

In some instances, the BILINUCB algorithm (Algorithm 2 of FIG. 4) is employed. In this aspect, the decision process uses linear UCB (e.g. bandit) but any imputation mechanism can be used, e.g., k-means, GCN, random, and the like. Thus, in some cases, the making of the decision includes applying a linear upper confidence bound bandit and the imputation includes a bounded imputation.

In some embodiments, the GCNUCB algorithm (Algorithm 3 of FIG. 5) is utilized. Thus, in some embodiments, making the decision includes retrieving a graph convolutional network embedding of the feature vector and providing same to a linear upper confidence bound bandit to make the decision; imputing the environmental feedback via the online imputation method includes applying the graph convolutional network; and the updating includes updating the linear upper confidence bound bandit with the environmental feedback and updating the graph convolutional network with the environmental feedback and the results of the online imputation method.

Figure 9:
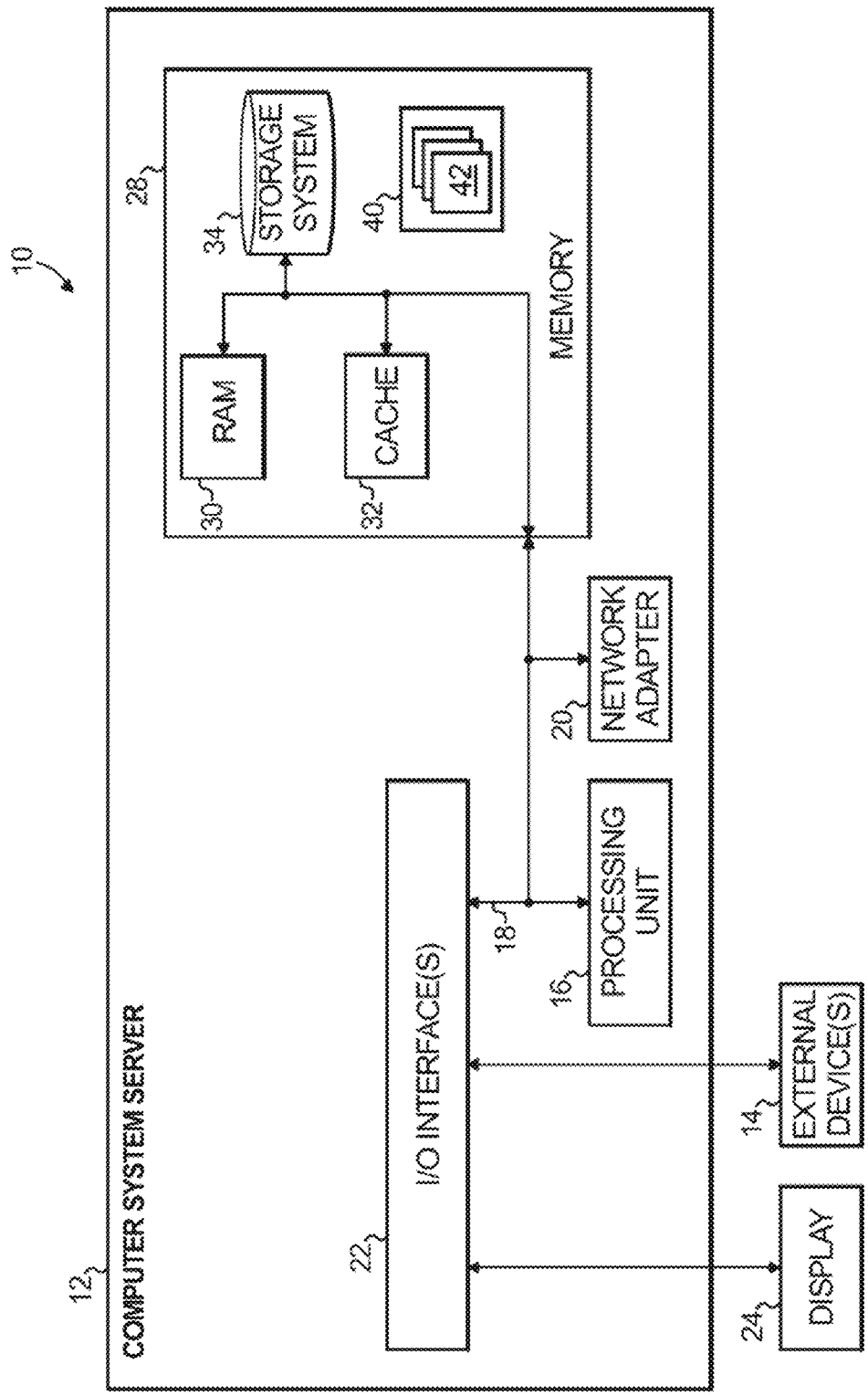
FIG. 9 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 9 depicts a computer system that may be useful in implementing one or more aspects and/or elements of the invention, also representative of a cloud computing node according to an embodiment of the present invention. Referring now to FIG. 9, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that May be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCT) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc. Communication with devices such as microphones or other transducers, medical diagnostic instruments, etc., can be, for example, via Input/Output (PO) interfaces 22 and/or via network adapter 20.

Thus, one or more embodiments can make use of software running on a general purpose computer or workstation. With reference to FIG. 9, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing, devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 9) running a server program. It will be understood that such a physical server may or may not include a display and keyboard.

One or more embodiments can be at least partially implemented in the context of a cloud or virtual machine environment, although this is exemplary and non-limiting.

Reference is made back to FIGS. 1-2 and accompanying text. Consider, e.g., a machine learning as a service app in layer 66 which implements at least a portion of online partially rewarded learning techniques as disclosed herein.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon., and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    obtaining a feature vector characterizing a system to be analyzed via online partially rewarded machine learning;
    based on said feature vector, making a decision, via said machine learning, using an online policy;
    observing said system for environmental feedback;
    in at least a first instance, wherein said observing indicates that said environmental feedback is available, obtaining said environmental feedback;
    in at least a second instance, wherein said observing indicates that said environmental feedback is missing, imputing said environmental feedback via an online imputation method;
    updating said online policy based on results of said obtained environmental feedback and said online imputation method; and
    outputting a decision based on said updated online policy.

2. The method of claim 1, wherein said system comprises a medical system conducting clinical trials.

3. The method of claim 1, wherein said system comprises a human-machine dialog system.

4. The method of claim 1, wherein said system comprises a medical diagnostic system.

5. The method of claim 1, wherein said imputing and said making of said decision comprise applying a rewarded online graph convolutional network by updating weights of said online policy via graph convolutional network back-propagation.

6. The method of claim 1, wherein said making of said decision comprises applying a linear upper confidence bound bandit and wherein said imputation comprises a bounded imputation.

7. The method of claim 1, wherein:
    making said decision includes retrieving a graph convolutional network embedding of said feature vector and providing same to a linear upper confidence bound bandit to make said decision;
    imputing said environmental feedback via said online imputation method comprises applying said graph convolutional network; and
    said updating comprises updating said linear upper confidence bound bandit with said environmental feedback and updating said graph convolutional network with said environmental feedback and said results of said online imputation method.

8. A non-transitory computer readable medium comprising computer executable instructions which when executed by a computer cause the computer to perform a method of:
    obtaining a feature vector characterizing a system to be analyzed via online partially rewarded machine learning;
    based on said feature vector, making a decision, via said machine learning, using an online policy;
    observing said system for environmental feedback;
    in at least a first instance, wherein said observing indicates that said environmental feedback is available, obtaining said environmental feedback;
    in at least a second instance, wherein said observing indicates that said environmental feedback is missing, imputing said environmental feedback via an online imputation method;
    updating said online policy based on results of said obtained environmental feedback and said online imputation method; and
    outputting a decision based on said updated online policy.

9. The non-transitory computer readable medium of claim 8, wherein said system comprises a medical system conducting clinical trials.

10. The non-transitory computer readable medium of claim 8, wherein said system comprises a human-machine dialog system.

11. The non-transitory computer readable medium of claim 8, wherein said system comprises a medical diagnostic system.

12. The non-transitory computer readable medium of claim 8, wherein said imputing and said making of said decision comprise applying a rewarded online graph convolutional network by updating weights of said online policy via graph convolutional network back-propagation.

13. The non-transitory computer readable medium of claim 8, wherein said making of said decision comprises applying a linear upper confidence bound bandit and wherein said imputation comprises a bounded imputation.

14. The non-transitory computer readable medium of claim 8, wherein:
    making said decision includes retrieving a graph convolutional network embedding of said feature vector and providing same to a linear upper confidence bound bandit to make said decision;
    imputing said environmental feedback via said online imputation method comprises applying said graph convolutional network; and
    said updating comprises updating said linear upper confidence bound bandit with said environmental feedback and updating said graph convolutional network with said environmental feedback and said results of said online imputation method.

15. An apparatus comprising:
    a memory; and
    at least one processor, coupled to said memory, and operative to:
        obtain a feature vector characterizing a system to be analyzed via online partially rewarded machine learning;

based on said feature vector, make a decision, via said machine learning, using an online policy;

observe said system for environmental feedback;

in at least a first instance, wherein said observing indicates that said environmental feedback is available, obtain said environmental feedback;

in at least a second instance, wherein said observing indicates that said environmental feedback is missing, impute said environmental feedback via an online imputation method;

update said online policy based on results of said obtained environmental feedback and said online imputation method; and output a decision based on said updated online policy.

16. The apparatus of claim 15, wherein said system to be analyzed is selected from the group consisting of a medical system conducting clinical trials and a medical diagnostic system.

17. The apparatus of claim 15, wherein said system comprises a human-machine dialog system.

18. The apparatus of claim 15, wherein said imputing and said making of said decision comprise applying a rewarded online graph convolutional network by updating weights of said online policy via graph convolutional network backpropagation.

19. The apparatus of claim 15, wherein said making of said decision comprises applying a linear upper confidence bound bandit and wherein said imputation comprises a bounded imputation.

20. The apparatus of claim 15, wherein:

making said decision includes retrieving a graph convolutional network embedding of said feature vector and providing same to a linear upper confidence bound bandit to make said decision;

imputing said environmental feedback via said online imputation method comprises applying said graph convolutional network; and said updating comprises updating said linear upper confidence bound bandit with said environmental feedback and updating said graph convolutional network with said environmental feedback and said results of said online imputation method.

* * * * *